US005962759A

United States Patent [19]
Gajda

[11] Patent Number: 5,962,759

[45] Date of Patent: Oct. 5, 1999

[54] MINIMIZING DIPHENYLETHANE FORMATION IN ALKYLATION OF BENZENE BY ETHYLENE CATALYZED BY ZEOLITE BETA

[75] Inventor: Gregory J. Gajda, Mt. Prospect, Ill.

[73] Assignee: UOP LLC, Des Plaines, Ill.

[21] Appl. No.: 08/841,982

[22] Filed: Apr. 8, 1997

Related U.S. Application Data

[63] Continuation-in-part of application No. 08/600,213, Feb. 12, 1996, abandoned.

[51] Int. Cl.$^6$ .................................................. C07C 2/54

[52] U.S. Cl. ........................................ 585/467; 585/446

[58] Field of Search ................................. 585/467, 446

[56] References Cited

U.S. PATENT DOCUMENTS

| | | | |
|---|---|---|---|
| 4,870,408 | 10/1989 | Ratcliffe et al. | 585/467 |
| 4,876,408 | 10/1989 | Ratcliffe et al. | 585/467 |
| 4,891,458 | 1/1990 | Innes et al. | 585/323 |
| 4,973,780 | 11/1990 | Johnson et al. | 585/467 |
| 5,081,323 | 1/1992 | Innes et al. | 585/449 |
| 5,087,784 | 2/1992 | Primack et al. | 585/446 |
| 5,227,558 | 7/1993 | Shamshoum et al. | 585/446 |
| 5,324,877 | 6/1994 | West et al. | 585/467 |
| 5,723,710 | 3/1998 | Gajda et al. | 585/467 |

*Primary Examiner*—Walter D. Griffin
*Assistant Examiner*—Nadine Preisch
*Attorney, Agent, or Firm*—Thomas K. McBride; Frank S. Molinaro

[57] ABSTRACT

Reduction of the amount of 1,1-diphenylethane and heavier polyalkylated benzenes produced in the formation of ethylbenzene by alkylation of benzene with ethylene can be effected by treating a non-templated zeolite beta at thermal oxidation conditions. The precursor zeolite beta contains at least 0.5% carbon which represents a combination of coke and high molecular organic compounds which are not removed by an extended benzene wash at about 200–250° C. The improvement leads to a product containing less than 0.3 weight percent 1,1-diphenylethane relative to ethylbenzene.

9 Claims, No Drawings

MINIMIZING DIPHENYLETHANE FORMATION IN ALKYLATION OF BENZENE BY ETHYLENE CATALYZED BY ZEOLITE BETA

CROSS REFERENCE TO RELATED APPLICATION

This application is a continuation-in-part of my copending application Ser. No. 08/600,213, filed Feb. 12, 1996 now abandoned, all of which is incorporated hereby.

BACKGROUND OF THE INVENTION

This application relates to a new form of zeolite beta and to its use as a catalyst in the alkylation of aromatics. More particularly, this application relates to a zeolite beta which shows substantially greater selectivity when used in the alkylation of benzene by ethylene. It is contemplated that the catalyst of this invention will be particularly valuable in production of high purity ethylbenzene, in minimizing formation of the diphenylethane which accompanies benzene alkylation by ethylene and in maximizing benzene utilization.

Ethylbenzene is the major article of commerce which is commonly made by the alkylation of benzene with ethylene. As is usual, several byproducts accompany ethylbenzene formation; a simplified summary of alkylation processes and products commonly occurring are given below.

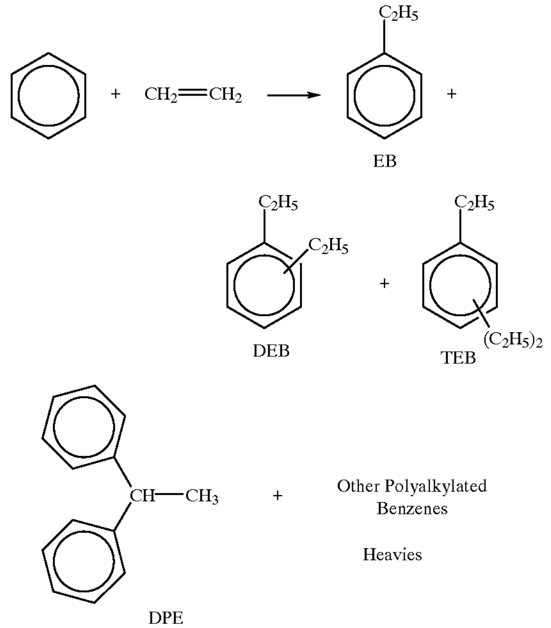

EB DEB TEB DPE

Zeolite beta has been found to be an effective catalyst and has gained a prominent role in the alkylation of benzene by ethylene. Although the formation of isomeric diethylbenzenes and triethylbenzenes might, at first glance, be viewed as byproducts representing a loss of ethylene, hence a reduction in efficiency of ethylene utilization, in fact each can be readily transalklylated to afford ethylbenzene as the sole alkylated benzene.

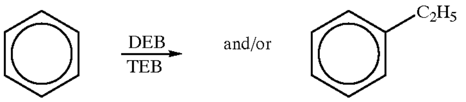

and/or

In contrast, diphenylethane can not be converted to ethylbenzene via alkylation and thus represents a loss of ethylene and a reduction in ethylene utilization efficiency. In fact, the coproduction of diphenylethane and polyalkylated benzenes, where the latter are collectively known as heavies, represents virtually all of the reduction in ethylene utilization.

Where Y zeolite is used as a catalyst in the reaction of ethylene and benzene approximately 0.65% DPE and about 0.55 weight percent of heavies are formed, resulting in a total loss of about 1.2%. Where zeolite beta is used only about 0.4% DPE and about 0.1% heavies are formed, resulting in a loss of 0.5%. Although this improvement is small it also is very significant, resulting in zeolite beta gaining favor as a catalyst of choice for ethylbenzene production. However, formation of even the latter small amount of DPE and heavies is vexing and gave impetus to further research whose goal was to reduce losses still further.

In the course of these investigations it was observed that a zeolite beta subjected to a carbon burn, or conditions of a carbon burn, afforded product with a significant reduction in DPE content. This result not only was serendipitous and surprising but also was not predictable from any known property of zeolite beta. This result was reproducible and forms the basis for our invention. A process of alkylating benzene with ethylene using the catalyst of this invention shows a significant selectivity advantage over one using untreated zeolite beta as the catalyst.

Our working hypothesis for the underlying chemistry responsible for the observed results is that when zeolite beta is subjected to a carbon burn, or conditions of a carbon burn, there is a selective loss of sites effecting hydride transfer reactions. Consequently, such a modified zeolite beta leads to reduced hydride transfer and products associated with hydride transfer. One general class of such products is the formation of diarylalkanes as a byproduct of virtually all aromatic alkylations by olefins. Thus, in the alkylation of benzene with ethylene there is reduced formation of diphenylethane. Another general class of such products are the n-alkylaromatics formed in the alkylation of aromatics with olefins. This is exemplified by a reduction in n-propylbenze formation accompanying alkylation of benzene by propylene. Yet another result which can be anticipated from our hypothesis is a reduction in phenylcyclohexane formation accompanying any alkylation of benzene. Cyclohexane is a common impurity in benzene, and hydride transfer during benzene alkylation can lead to formation of cyclohexene. The latter serves as an active alkylating agent and reacts with benzene to form phenylcyclohexane. The outcome of the foregoing hypothesis and its logical consequences is that one can expect the catalyst of this invention with reduced hydride transfer sites to confer benefits generally upon the alkylation of aromatics with olefins.

Another outcome of our hypothesis is that any method leading to a reduction in hydride transfer sites of a zeolite beta affords material useful in the process of our invention. Defining for the purpose of this invention a "site-modified zeolite beta" as one which has fewer hydride transfer sites than a native, untreated zeolite beta, clearly effecting a carbon burn is but one method of producing such a site-modified zeolite beta. Another method of achieving similar results is to calcine zeolite beta for extended times in a steam atmosphere at a temperature in excess of 675° C.

Ratcliffe, U.S. Pat. No. 4,876,408, previously has used a carbon burn for several zeolites, including zeolite beta, to modify the catalyst so as to increase its selectivity for monoalkylation by at least 1.0 percentage point. On contrast to the Ratcliffe catalyst, our site-modified zeolite beta decreases monoalkylation selectivity, an observation which is certainly unexpected in view of the contrary prior art teaching! It also is not obvious that a decrease in monoalkylation would be desirable, or even tolerable. However, as we discussed earlier, we recognize that the critical feature in alkylation is minimizing diphenylethane formation, which our catalyst accomplishes more effectively than the prior art catalysts.

Although Shamshoum et al. have taught a steam-modified zeolite beta for aromatic alkylation in U.S. Pat. No. 5,227,558, their catalyst is functionally quite distinct from ours, as will become apparent in our presentation of experimental data. The patentees' catalyst also has a significantly higher ratio of silica to alumina than the catalysts taught herein—and outside the range we believe important to the success of our invention!.

SUMMARY OF THE INVENTION

A purpose of this invention is to produce ethylbenzene by the alkylation of benzene with ethylene in a process which forms 1,1-diphenylethane and polyalkylated benzenes which can not be transalkylated with benzene to ethylbenzene (heavies) in an amount of 0.3 weight percent or less based on ethylbenzene formation. An embodiment comprises the use in the alkylation of benzene by ethylene of a non-templated zeolite beta as a catalyst arising from a zeolite beta having at least 0.1 weight percent carbon deposited thereon which has been subjected to oxidation at 450 to about 750° C. In a more specific embodiment the zeolite beta which is subjected to thermal oxidation contains at least 1% carbon. In another embodiment the site-modified zeolite beta is prepared by steam calcination at 675° C. to about 850° C. and contains a silica to alumina ratio no greater than about 30. Other purposes and embodiments will become clear from the ensuing description.

DESCRIPTION OF THE INVENTION

Although conventional zeolite betas give excellent results in the alkylation of benzene by ethylene to produce ethylbenzene there remain small but significant losses arising from the formation of both 1,1-diphenylethane and polyalkylated materials (heavies) which can not be transalkylated with benzene to afford ethylbenzene. The formation of heavies is chemically readily apparent; the formation of DPE appears anomalous but probably results from hydrogen transfer in chemisorbed ethylbenzene to ethylene with formation of chemisorbed styrene which then serves to alkylate benzene; vide supra. This is summarized in the following reaction.

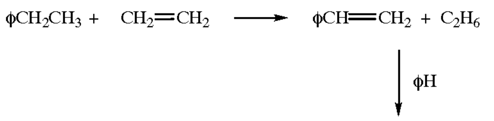

-continued

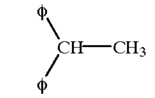

It is known that the amount of DPE formed depends on the ethylene:benzene ratio according to the formula $$[DPE] \approx [E/B]^2$$

Thus, increasing this ratio (or conversely, decreasing the B/E ratio, since the reaction typically is run at B/E>>1) increases the amount of DPE formed, which is undesirable. However, one prefers to carry out the reaction at as high a ratio of ethylene to benzene to reduce the utilities cost associated with the recovery of excess benzene, which conflicts directly with the desire to minimize DPE production. Thus, it is doubly imperative to increase the selectivity—as measured by DPE and heavies production—of a zeolite beta catalyst.

Quite fortuitously we observed that when a catalyst with substantial process usage is subject to conditions of a carbon burn and returned to service there was a significant decrease in both the amount of DPE and heavies formed as byproducts. This observation is unprecedented, is completely unexpected, and forms the basis of the present invention.

The invention described within is particularly applicable to the liquid phase alkylation of benzene with ethylene. The molar ratio of benzene to ethylene is in the range of 8:1 to about 1:1, although the alkylation is more generally performed at a molar ratio between about 6:1 to as low as 3:1. As stated previously, a lower ratio is desirable from the aspect of lowering utilities cost, but is undesirable in that it leads to more DPE formation. However, as discussed above our invention can be expected to be generally applicable to the alkylation of aromatics with olefins. Although benzene is the principal aromatic of interest, aromatics such as alkyl-substituted benzenes, condensed ring systems generally and alkylated derivatives thereof may be used. Exemplary of such materials are toluene, ethylbenzene, propylbenzene, and so forth; xylene, mesitylene, methylethylbenzene and so on; naphthalene, anthracene, phenanthrene, methylnaphthalene, dimethyinaphthalene, and tetralin. Although the lower olefins, i.e., those having 2–6 carbon atoms, are the principal alkylating agents contemplated olefins in the C2–C20 range may be effectively used in the practice of our invention. In general, the molar ratio of olefin to aromatic is within the range of 15:1 to about 1:1, and generally is under about 8:1.

The alkylation is performed in the liquid phase. Consequently, reaction pressures need to be sufficiently high to ensure at least a partial liquid phase. A pressure between about 200 and 1,000 psig (1379–6985 kPa) constitutes the usual pressure interval under which alkylation is run, where ethylene is the olefin, although more commonly it is carried out at a pressure between 300 and 600 psig (2069–4137 kPa), with the range between 450 and 600 psig (3103–4137 kPa) even more commonly used. However, it needs to be emphasized that pressure is not a critical variable in the success of our invention and the only criterion is that the pressure be sufficiently great to ensure at least partial liquid phase. In the general case our invention may be practiced at a pressure between about 50 psig (345 kPa) and 1000 psig. The alkylation reaction between benzene and ethylene typically is performed at a temperature between about 200 and about 260° C., more preferably in the interval 230–250° C., and at a liquid hourly space velocity, based on ethylene, between about 0.1 and about 1.5 per hour. For other olefins the appropriate reaction temperature is in the range 100–425° C.

The catalyst of our invention is derived from a non-templated zeolite beta which contains at least 0.5% carbon, and preferably at least 1% carbon. What is meant by the phrase "1% carbon on the catalyst" is that there is 1 weight percent carbon on the catalyst as determined by combustion analysis to generate CO and $CO_2$ using a LECO analyzer. More generally, the catalyst prior to oxidation will contain 0.5 to about 10 weight percent carbon, and more usually will contain from about 1 up to about 5 weight percent carbon. The non-templated zeolite beta precursor initially has a great deal of organic material, and possibly coke, impregnated thereon. In order to remove the lighter organic materials it is typically washed with benzene for 24 hours at 200–250° C. However, any aromatic capable of entering the zeolite beta channels may be used as a wash solvent, and the aromatic also may contain up to about 30 weight percent of saturated hydrocarbons. This wash removes all lighter materials so that only coke and higher molecular weight organic materials remain in the pores. Such higher molecular weight organic materials include polyalkylated compounds and ethylene oligomers. This precursor non-templated zeolite beta is then subject to thermal oxidation. Such conditions include a temperature between about 450 and 750° C., preferably between 600 and 700° C. for a time between about 1 and about 10 hrs. in an oxidative atmosphere. Most usually the oxidative atmosphere is air, although this is not a requirement. Any atmosphere containing at least about 0.5% oxygen will suffice as the oxidative atmosphere in our invention. The oxidation normally is performed with air flowing over the zeolite beta at a rate between 10 and 1000 SCFH/percent of catalyst (measured on a volatile-free basis), with rates of 20–30 SCFH/percent catalyst usually being sufficient. It is critical to note that our catalysts, prepared according to the foregoing method, do not afford an increase in monoalkylation selectivity, but in fact effects alkylation with decreased monoalkylation selectivity.

Another method of making the site-modified zeolite beta of this invention is to calcine a zeolite beta, templated or not, for extended times at over 675° C. up to about 850° C., in a steam atmosphere. More specifically, a calcination time of at least 6 hours is necessary at temperatures below 700° C., although as the temperature increases to 750° C. the calcination time may be decreased to about 3 hours. It is important that the calcination be done in a steam atmosphere, especially in an atmosphere containing from about 5 up to about 25 weight percent water. The resulting steam calcined zeolite beta has a silica to alumina ratio which is no greater than about 30.

As stated previously, in the alkylation of benzene with ethylene using our site-modified zeolite beta as catalyst there is a significant reduction in the amount of 1,1-diphenylethane and polyalkylated benzenes which cannot be transalkylated to benzene ("heavies") formed as byproducts. In particular, our process affords less than 0.3 weight percent of the 1,1-diphenylethane plus heavies relative to ethylbenzene, which is an important improvement over prior art results. Another critical feature of our catalysts is that there is decreased selectivity with respect to monoalkylation. Another characteristic of the site modified zeolite beta catalysts of our invention is that in the alkylation of benzene with ethylene, the diethylbenzenes are formed with a meta:para ratio greater than 1.25, preferably greater than 1.5, and most preferably greater than 1.8. In a particularly desirable variant, the ortho:para ratio is less than 0.75, preferably under 0.6, and most preferably less than 0.5. In general, alkylation of benzene by olefins using as a catalyst the site-modified zeolite beta of our invention affords dialkylbenzenes having a meta:para ratio greater than 1.25, and in a desirable variant an ortho:para ratio less than 0.75.

The alkylation of aromatics by olefins catalyzed by the catalyst of our invention may be carried out in any of the ways which are well known to those practicing the art. For example, the process in general can be carried out in a batch mode by heating the catalyst, an aromatic represented by benzene, and an olefin as ethylene in a stirred autoclave at a temperature between about 200 and 260° C. and at a pressure sufficient to maintain at least a partial liquid phase. The pressure typically will be in the range of 200 to about 1,000 psig, but again we emphasize that the pressure requirements are not restrictive but serve only to ensure at least partial liquid phase reaction.

However, the process is more advantageously performed in the continuous mode employing a fixed bed reactor operating in an upflow or downflow mode or using a moving bed reactor operating with cocurrent or countercurrent catalyst and hydrocarbon flows. The reactors also may contain one or more catalyst beds and may be equipped for the interstage addition of olefin as well as interstage cooling. Interstage olefin addition assures a more nearly isothermal operation and tends to enhance product quality and catalyst life. A moving bed reactor provides the advantage of continuous spent catalyst removal for regeneration and replacement by fresh or regenerated catalyst. However, it also is possible to carry out our invention using swing bed reactors. As yet another common variant which may be used in the practice of our invention may be mentioned effluent recycle. Thus, effluent may be recycled and mixed with fresh feed in order to ensure efficient utilization of reactants without the necessity of their separation from the reactor effluent.

The following examples are only illustrative of our invention which is not limited thereby.

EXAMPLES

Preparation of zeolite betas. Zeolite beta was prepared in accord with the description in U.S. Pat. No. 5,139,759. Powdered zeolite beta was washed using as the wash solution an aqueous solution containing 1.0 lb $NH_4NO_3$ and 0.252 lb $HNO_3$ per pound dry weight of zeolite. The mixture of beta and wash solution were held at 85° C. for 1 hour. Solid was separated, washed well with water, air dried overnight, then dried at 200° F. (93° C.) to equilibrium. The dried zeolite was used as an extrudate which was calcined at a maximum bed temperature of 675° C. for about 3 hours. This material is designated as catalyst A in the table below.

The foregoing material was utilized as a catalyst in the alkylation of benzene by ethylene. After service it was washed with flowing benzene at 4 LHSV at 240° C. for 24 hours. The cooled catalyst was purged with hydrogen to remove residual benzene, then carbon-burned by ramping from ambient temperature to 650° C. in 3 hours; holding at 650° C. for 3 hours, then cooled to room temperature to afford catalyst B. Air was flowing over the catalyst at ambient pressure at a rate of ca. 5 standard liters per minute.

Alkylation of benzene with ethylene using zeolite betas. Approximately 20 g of catalyst was loaded into a ⅝" ID reactor and sand-packed to minimize channeling. Feeds were passed upflow through the reactor and a reactor effluent recycle ratio of 3:1 (recycle rate relative to total benzene feed rate) was used to control the size of the exotherm. All of the olefin was mixed with the feed benzene at the reactor inlet. Other operating conditions are given in the Table.

The following table summarizes the results observed after the reactor had lined out and stabilized, i.e., after a steady state had been reached.

TABLE 1

Comparison of Original and Treated Catalysts

| Catalyst | A | B |
|---|---|---|
| Temp, C | 240.7 | 241.8 |
| Benzene LHSV | 2.9 | 3.3 |
| Pressure, psig | 549 | 545 |
| Benzene/Ethylene (molar) | 4.59 | 4.43 |
| Selectivities, % | | |
| Ethylbenzene | 89.08 | 84.77 |
| m-DEB | 6.08 | 7.97 |
| p-DEB | 2.80 | 3.82 |
| o-DEB | 0.59 | 1.64 |
| TEB | 0.94 | 1.62 |
| DPE | 0.31 | 0.13 |
| Heavies | 0.19 | 0.03 |
| Others | 0.01 | 0.02 |
| DPE/EB, % | 0.347 | 0.156 |
| C2 = Efficiency, % | 99.38 | 99.72 |

What is claimed is:

1. A process for making ethylbenzene comprising alkylating in the liquid phase benzene with ethylene in a molar proportion ratio from 1 up to about 8 at a temperature from about 200° C. up to about 260° C. and at a pressure sufficient to maintain at least a partial liquid phase, in the presence of a site-modified zeolite beta catalyst, selected from the group consisting of (a) a site-modified beta resulting from heating at a temperature from about 450° C. to about 750° C. in the presence of a flowing oxygen-containing stream, a non-templated first zeolite beta having at least 0.5 wt. % carbon deposited thereon and (b) a site-modified zeolite beta resulting from calcining a zeolite beta at a temperature from about 675° C. up to about 850° C. in an atmosphere containing from about 5 up to about 25 wt. % water, and has a silica alumina ratio no more than about 30.

2. A process for preparing a monoalkylated benzene comprising alkylating in the liquid phase benzene with an olefin in a molar proportion ratio from 1 up to about 15 at a temperature from about 100° C. up to about 425° C. and at a pressure sufficient to maintain at least a partial liquid phase, in the presence of a site-modified zeolite beta catalyst, selected from the group consisting of (a) a site-modified beta resulting from heating at a temperature from about 450° C. to about 750° C. in the presence of a flowing oxygen-containing stream, a non-templated first zeolite beta having at least 0.5 wt. % carbon deposited thereon and (b) a site-modified zeolite beta resulting from calcining a zeolite beta at a temperature from about 675° C. up to about 850° C. in an atmosphere containing from about 5 up to about 25 wt. % water, and has a silica:alumina ratio no more than about 30.

3. The process of claim 1 where the molar proportion of benzene to ethylene is between about 3 and about 6.

4. The process of claim 1 where the reaction temperature is from about 230 to about 250° C.

5. The process of claim 1 where the pressure is from about 450 to about 600 psig.

6. The process of claim 1 where the first zeolite beta catalyst has from about 0.5 to about 10 weight percent carbon deposited thereon prior to being heated in a flowing oxygen-containing stream.

7. The process of claim 2 where the olefin has from 2 up to about 20 carbon atoms.

8. The process of claim 7 where the olefin has from 2 up to about 6 carbon atoms.

9. The process of claim 2 where the first zeolite beta catalyst has from about 0.5 to about 10 weight percent carbon deposited thereon prior to being heated in a flowing oxygen-containing stream.

* * * * *